(12) United States Patent
Stewart et al.

(10) Patent No.: US 8,372,614 B2
(45) Date of Patent: Feb. 12, 2013

(54) ETHANOL PRODUCTION FROM SOLID CITRUS PROCESSING WASTE

(75) Inventors: David Stewart, Boca Raton, FL (US); Wilbur W. Widmer, Winter Haven, FL (US); Karel Grohmann, Davenport, FL (US); Mark Wilkins, Stillwater, OK (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 1607 days.

(21) Appl. No.: 11/784,719

(22) Filed: Apr. 9, 2007
(Under 37 CFR 1.47)

(65) Prior Publication Data
US 2008/0213849 A1   Sep. 4, 2008

Related U.S. Application Data

(63) Continuation-in-part of application No. 11/052,620, filed on Feb. 7, 2005, now abandoned.

(51) Int. Cl.
    *C12P 7/06*    (2006.01)
    *C12P 7/12*    (2006.01)
    *C12P 7/08*    (2006.01)
    *C12P 7/14*    (2006.01)
(52) U.S. Cl. ........ 435/164; 435/161; 435/162; 435/163; 435/262; 435/410; 435/243
(58) Field of Classification Search .............. 435/161, 435/162, 163, 164, 410, 243, 262
    See application file for complete search history.

(56) References Cited

U.S. PATENT DOCUMENTS

| | | | |
|---|---|---|---|
| 1,973,084 A | 9/1934 | Lewis | |
| 2,276,420 A | 3/1942 | Rosenfeld et al. | |
| 2,471,893 A | 5/1949 | Pulley | |
| 2,625,488 A | 6/1950 | Wasserman et al. | |
| 2,561,072 A | 7/1951 | Reich | |
| 3,745,020 A | 7/1973 | Lime et al. | |
| 3,862,014 A | 1/1975 | Atkins et al. | |
| 3,966,984 A | 6/1976 | Cocke et al. | |
| 4,113,573 A | 9/1978 | Gerow | |
| 4,291,124 A | 9/1981 | Muller et al. | |
| 4,313,372 A | 2/1982 | Gerow et al. | |
| 4,326,926 A | 4/1982 | Gerow | |
| 4,334,962 A | 6/1982 | Gerow | |
| 4,488,912 A | 12/1984 | Milch et al. | |
| 4,490,469 A | 12/1984 | Kirby et al. | |
| 4,497,838 A | 2/1985 | Bonnell | |
| 4,503,079 A | 3/1985 | King et al. | |
| 4,547,226 A | 10/1985 | Milch et al. | |

(Continued)

OTHER PUBLICATIONS

Jacques, K., et al., "Ethanol Distillation: The Fundamentals", *The Alcohol Textbook*, 2003, pp. 325-326.

(Continued)

*Primary Examiner* — Nathan Bowers
(74) *Attorney, Agent, or Firm* — John D. Fado; G. Byron Stover

(57) ABSTRACT

Method for producing ethanol from solid citrus waste by reducing the concentration of limonene in citrus waste to allow fermentation. In one embodiment ground solid citrus waste is partially hydrolyzed and pasteurized by heating using a jet cooker and then injected into a flash tank to remove limonene. The heated citrus waste is then cooled, hydrolyzed with enzymes and fermented to ethanol. The remaining solids and liquids may be processed further to yield other byproducts. More particularly, the solids may be dried and pressed for use in cattle feed and the liquids may be further fermented or processed to yield additional ethanol, acetate, galacturonic acid monomers and polymers, five carbon sugars and other products.

26 Claims, 3 Drawing Sheets

U.S. PATENT DOCUMENTS

| | | | |
|---|---|---|---|
| 4,564,595 | A | 1/1986 | Neves |
| 4,637,835 | A | 1/1987 | Nagle |
| 4,650,689 | A | 3/1987 | Hedrick |
| 4,818,250 | A | 4/1989 | Whitworth |
| 4,915,707 | A | 4/1990 | Whitworth |
| 4,938,985 | A | 7/1990 | Swaine, Jr. et al. |
| 4,952,504 | A | 8/1990 | Pavilon |
| 4,971,813 | A | 11/1990 | Strobel et al. |
| 4,973,485 | A | 11/1990 | Rich |
| 5,100,679 | A | 3/1992 | Delrue |
| 5,135,861 | A | 8/1992 | Pavilon |
| 5,198,074 | A | 3/1993 | Villavicencio et al. |
| 5,259,945 | A | 11/1993 | Johnson, Jr. et al. |
| 5,470,478 | A | 11/1995 | Leva |
| 5,571,703 | A | 11/1996 | Chieffalo et al. |
| 5,628,830 | A * | 5/1997 | Brink .............................. 127/36 |
| 5,915,815 | A | 6/1999 | Moore et al. |
| 6,076,362 | A | 6/2000 | Hubinger et al. |
| 6,143,337 | A | 11/2000 | Fishman et al. |
| 6,151,799 | A | 11/2000 | Jones |
| 6,183,806 | B1 | 2/2001 | Ficca et al. |
| 6,251,643 | B1 | 6/2001 | Hansen et al. |
| 6,267,309 | B1 | 7/2001 | Chieffalo et al. |
| 6,753,028 | B2 | 6/2004 | Iada et al. |
| 6,766,595 | B2 | 7/2004 | Anderson |
| 6,962,722 | B2 | 11/2005 | Dawley et al. |
| 7,060,313 | B2 | 6/2006 | Jones |
| 2002/0031581 | A1 | 3/2002 | Baker, IV |
| 2004/0063184 | A1 | 4/2004 | Grichko |
| 2004/0091983 | A1 | 5/2004 | Veit |
| 2004/0170731 | A1 | 9/2004 | Subramaniam et al. |
| 2004/0253696 | A1 | 12/2004 | Grichko |
| 2005/0054064 | A1 | 3/2005 | Talluri |
| 2006/0154352 | A1 | 7/2006 | Foody et al. |
| 2006/0177916 | A1 | 8/2006 | Stewart |
| 2007/0082385 | A1 | 4/2007 | Smith et al. |
| 2007/0190620 | A1 | 8/2007 | Mueller |
| 2008/0227166 | A1 | 9/2008 | Allain et al. |

OTHER PUBLICATIONS

McDonald, K., et al., "Vacuum Cooling Technology for the Food Processing Industry: A Review", *J. of Food Engineering*, vol. 45, 2000, pp. 55-65.

www.floridachemical.com/whatisd-limonene.htm.

Grohmann, K., et al., "Production of Ethanol from Enzymatically Hydrolized Orange Peel by the Yeast Saccharomyces cervisiae", Applied Biochemistry and biotechnology, vol. 45/46. pp. 315-327, 1994.

Grohmann, K., et al., "Fermentation of Sugars in Orange Peel Hydrolysates to Ethanol by recombinant *Escherichia coli* KO11", Applied Biochemistry and biotechnology, vol. 51/52, pp. 423-435, 1995.

Gerow, G., "Economics of d-limonene recovery", Transcript of the 1974 citrus Engineering conf., ASME, vol. 20, 1974, pp. 61-66.

Kesterson, J.W., et al., "By-Products and Specialty Products of Florida Citrus", Institute of food and Agricultural Sciences, Dec. 1976, 2003, pp. 8, 102, and many others.

Pan, X., et al., "Strategies to Enhance the Enzymatic Hydrolysis of Pretreated softwood with High Residual Lignin Content", Applied Biochemistry and biotechnology, vol. 121-124, 2005.

Kelsall, D., et al., "Grain dry milling and cooking procedures: extracting sugars in preparation for fermentation", The Alcohol Textbook, 2003, pp. 17-19.

Kling, S., et al., "Enhancement of Enzymatic Hyrolysis of Sugar Cane Bagasse by steam Explosion Pretreatment", Biotechnology and Bioengineering, vol. 19, 1987, pp. 1035-1039.

Philippidis, G., et al., "Study of the Enzymatic Hydrolysis of cellulose for Production of Fuel Ethanol by the Simultaneous Saccharification and fermentation Process", Biotechnology and Bioengineering, vol. 41, 1993, pp. 846-853.

Lane, A.G., 1980, Journal Chem. Tech. Biotechnol., 30, pp. 345-350.

Mizuki, E., Akao, T., and Saruwatari, T., 1990, Biol. Wastes, 33, pp. 161-168.

* cited by examiner

US 8,372,614 B2

ETHANOL PRODUCTION FROM SOLID CITRUS PROCESSING WASTE

REFERENCE TO RELATED APPLICATION

This application claims the benefit of U.S. patent application Ser. No. 11/052,620, filed 7 Feb. 2005, which is incorporated herein by reference in its entirety.

BACKGROUND OF THE INVENTION

This invention relates to citrus waste processing and, more particularly, a method for the conversion of simple and complex carbohydrates contained in solid citrus waste into ethanol for use as bio-fuel and to yield other high-value byproducts.

Currently, the generation of solid citrus waste, consisting primarily of peel, membranes, and seeds, which result from the processing of citrus fruit for juice, is an environmental problem. The problem exists particularly in areas where the bulk of citrus is grown to produce juice, such as in the State of Florida and the country of Brazil. For example, Florida in 2003 had approximately 103 million citrus trees on 800,000 acres and produced 297 million boxes of citrus, 85% of which was processed into juice. The waste from such processing was approximately one-half of the citrus fruit, yielding approximately 5 million tons of wet solid waste which reduces to 1.2 million tons of dry waste. While raw wet solid citrus waste contains between 76-82% water, the spongy structure of the citrus waste and the high content of polysaccharides in the form of pectin, cellulose and hemicellulose binds this water so the solid citrus waste material consists of solid pieces with no free liquid between the solid pieces. The composition of citrus waste is approximately 5-8% simple sugars (e.g., fructose, glucose, sucrose), 3-5% pectin, 2-3% cellulose, 2-3% hemicellulose, 1-2% flavonoids, 1% organic acids, 1% protein, 1% ash, and 1% oil. Traditionally, such solid citrus waste has been converted into cattle feed which typically does not have sufficient value to cover the production and transportation costs associated therewith. A further drawback of converting current citrus waste into cattle feed is that the waste contains a high amount of d(+)-limonene (generally referred to simply as limonene). Volatilization of the limonene during the drying process causes air pollution to the extent that limonene vapors are exhausted into the atmosphere at the processing plants, this happens because it would require very expensive equipment to trap the limonene from the drier exhaust. Although citrus waste materials do create an environmental problem, these materials are rich in pectin and other polysaccharides that can be hydrolyzed into sugars for use in the production of ethanol.

Currently ethanol is used as a bio-fuel that is mixed with gasoline to increase the octane rating and improve the environmental characteristics of gasoline. Although another gasoline octane enhancer referred to as MTBE (Methyl Tertiary Butyl Ether) is also used, utilization of MTBE is controversial since it is not biodegradable, results in ground water pollution and for these reasons its use has already been banned in more than 17 states with more states expected to follow. Field corn (maize) is currently the primary feedstock for ethanol production in the USA. As the State of Florida has no cultivation of field corn, Florida must look to other sources for producing ethanol. The conversion of solid citrus processing waste into ethanol would reduce waste and provide a regional source of ethanol as a viable alternative octane enhancer to MTBE. The conversion of citrus processing waste in 2003 of approximately 5 million tons could result in potentially 100 million gallons of ethanol.

A major problem that prevents processing citrus waste into ethanol using microorganisms is limonene. Limonene is a liquid terpene that is contained in citrus peel. Limonene provides a natural defense for the fruit against bacteria, viruses, molds, and other organisms. Accordingly, limonene helps to protect the citrus waste from microbial buildup and fermentation by normal processes that would yield ethanol. It is also desirable to recover the limonene as a high value co-product. For efficient fermentation, limonene in the citrus waste must be reduced to a level below 3000 parts per million (preferred level below 1500 ppm) from the natural level of about 5,000-15,000 ppm. Another problem with fermentation of raw or pressed citrus waste is contamination with bacteria and other microorganisms which can take over the fermentation and divert it to products other than ethanol. Thus, a need exists for processes that will decrease the amount of limonene in citrus processing waste and sterilize or pasteurize the waste in order to produce ethanol for use as a bio-fuel and also to produce other high value products, including cattle feed, limonene, five carbon sugars and galacturonic acid monomers and polymers.

Yet another problem is the release of fermentable sugars from citrus waste at concentrations as high as possible. Ethanol is produced at approximately 50 weight % yield based on sugars consumed, and the energy consumption for recovery of ethanol by distillation rapidly increases with decreasing ethanol concentration in fermented mixtures (mash). Dilution of solid citrus waste with large amounts of water often currently used to aid processing and to accommodate equipment limitations is thus not practical for ethanol production from this material. Citrus waste needs to be processed at high concentration of solids which makes handling and processing of the material very difficult; in addition, waste tissues need to be broken down to release soluble sugars and complex carbohydrates (e.g., pectin, cellulose, hemicellulose) must be hydrolyzed to release additional sugars and maximize ethanol production.

Some individual steps such as shredding, limonene removal, hydrolysis of the citrus waste, and fermentation of sugars to ethanol are known in the prior art. However, the prior art has not provided an integrated system or method which can process solid citrus waste with minimal dilution by water and which addresses all of the problems outlined above.

U.S. Pat. No. 4,503,079 (King) discloses a process for the production of ethanol from citrus press liquor and molasses. Citrus press liquor is a liquid product obtained by treating solid citrus waste with lime and pressing it to release the juices (citrus press liquor). The citrus press liquor is usually concentrated by evaporation to another liquid product called citrus molasses. The limonene contained in press liquor can be mostly removed during evaporation in overhead vapors as disclosed in U.S. Pat. No. 2,561,072 (Reich). King discloses removal of limonene (peel oil) from citrus press liquor by steam stripping at high temperatures (240°-260° F.), dilution of deoiled citrus molasses with water and fermentation of such deoiled, diluted molasses to ethanol. The process disclosed by King does not teach removal of limonene from solid citrus waste and is unsuitable for processing of such material since the equipment utilized by King is incapable of handling solid citrus waste. In addition the process disclosed by King is very inefficient in that it utilizes less than one half of the soluble fermentable sugars present in citrus waste as only those fermentable sugars present in the liquid portion that can be pressed from the waste are used and the press liquor yield is approximately one half of the total liquid contained in the citrus waste. None of the fermentable sugars in the complex carbohydrates are utilized by King because these carbohydrates are not hydrolyzed and released and made available for fermentation. The method described by King requires liquid streams and cannot handle solids or highly viscous materials whereas the present invention described herein can handle solid citrus waste and the entire citrus waste stream taking advantage of all the sugars present, including those in the form of complex carbohydrates.

Pavilon in U.S. Pat. Nos. 4,952,504 and 5,135,861 discloses a chemical method for hydrolysis of citrus waste at very high temperatures (400°-500° F.) and pressures (365-515 psia) using carbon dioxide (carbonic acid) or indigenous acids as catalysts. However, the process disclosed by Pavilon can only utilize and process the whole citrus waste biomass as a slurry in water; about one-fourth to one-third of a gallon of water (approximately 2-3 pounds) is added for each pound of peel. This method thus relies on addition of water and excessive dilution (3-4 fold) of the initial solid citrus waste material and results in a fermented material (mash) with ethanol contents of less than 1.5%. However, distillation costs to recover ethanol from such fermented mash with less than 4% ethanol by volume rise exponentially and quickly becomes prohibitively expensive (The Alcohol Textbook, 2003, K. A. Jacques, T. P. Lyons, D. R. Kelsall, Ed., Notingham University Press, Notingham, UK, p 326.). The method described by Pavilon requires slurries and cannot handle solids or highly viscous materials. Pavilon also discloses that the citric acid content present in citrus peel can be used to catalyze the hydrolysis of the pectin, cellulose and hemicellulose into simple sugars at the temperatures used. However, citric acid is not present in the waste as a free acid but as salts and the concentration of catalytic hydronium ions is too low (pH=4-5) for efficient hydrolysis of these complex polysaccharides; thus only incomplete hydrolysis is possible. Pavilon does not disclose removal of limonene prior to fermentation and instead relies on dilution of citrus waste with water to decrease limonene concentration in the fermentation step.

U.S. Pat. No. 6,251,643 (Hansen) discloses a process for hydrolysis of biomass (e.g., vegetable) using a multistage screw press to carry out the process. While the screw press reactor may be suitable for processing of fibrous vegetable matter, it is not suitable for processing of steam (vapor) treated citrus processing waste since such waste becomes extremely soft upon steaming and passes easily through screen openings even under very low pressure. Screen presses or similar filtering devices are thus unsuitable for dewatering of heat treated, wet highly viscous citrus waste. Hansen also relies on addition of large amounts of liquid (aqueous solutions) and subsequent pressing to accomplish heating, cooling and separation of vegetable matter prior to enzymatic hydrolysis. Such addition of water dilutes the concentration of sugars and ultimately ethanol. In addition, screw press devices are complex, consume large amounts of energy for pressing, and have high maintenance requirements. The present invention does not require separation of liquids and solids until the last steps, i.e. after fermentation or distillation have been completed; the recycling of large streams of liquid is thus avoided, equipment is simplified, and a more efficient method is provided.

The present invention disclosed herein utilizes all fermentable sugars, both free and those bound as complex carbohydrates (e.g., cellulose, hemicellulose, and pectin) using physical and chemical hydrolysis aided by enzymes and does not require addition of excessive amounts of water. The present invention provides a means of economically treating and handling solid citrus waste with minimal dilution so that the solids content of the original solid citrus waste substrate is reduced by less than about 25% (e.g., less than 25%; preferably less than about 10% (e.g., less than 10%), more preferably less than about 5% (less than 5%)), compared to the raw feed, to yield a substrate and means to handle the substrate with means of liquefying and fermenting such substrate that after fermentation yields a product containing about 4% to about 6% (e.g., 4-6%) ethanol from which the ethanol can be economically stripped to produce a beverage or fuel grade product. The added water comes only from the difference between the steam utilized and condensed in the jet cooker and the water evaporated during flashing of limonene and vacuum cooling. This typically amounts to addition of less than about 0.3 lbs (e.g., less than 0.3 lbs; 0.036 gallons) of water to each pound of added citrus waste, preferably addition of less than about 0.15 lbs (e.g., less than 0.15 lbs; 0.018 gallons), and more preferably less than about 0.1 lb water (e.g., less than 0.1 lbs; 0.01 gallons) for each pound of added solid citrus waste. This is at least 7 to 30 times less water addition than is necessary in the process described by Pavilon in U.S. Pat. Nos. 4,952,504 and 5,135,861.

The present invention disclosed herein, for processing solid citrus waste to ethanol, utilizes enzyme mixtures (e.g., pectinase, hemicellulases, cellulases and beta-glucosidases) for efficient hydrolysis of the complex carbohydrates in citrus waste residue into simple sugars with concurrent fermentation or hydrolysis followed by fermentation. It offers several advantages over the prior art. The process described by King does not utilize all of the sugars available (less than ⅓) in citrus waste as only the part of the liquid portion that can be pressed from the waste to produce press liquor and concentrated citrus molasses is used. The process described by Pavilon claims to utilize all the sugars in the waste stream but requires addition of excessive amounts of water to allow handling of the citrus waste and decrease inhibition by limonene, resulting in a fermented product with a dilute ethanol content under 1.5% which makes it substantially more costly to recover the ethanol.

Two different processes, (1) gas (e.g., flue gas, air) or steam stripping (preferred) or (2) centrifuging, can be used in the present invention to lower the limonene content in the citrus waste to a sufficiently low level whereby subsequent fermentation of the waste can efficiently produce ethanol. Steam stripping is most preferred as the waste does not have to be hydrolyzed or diluted with water as required for centrifuging, and the removed limonene may be easily collected and recovered by condensing the stripped water and limonene vapors with the limonene collecting on top of the water layer. The fermentation utilizes traditional ethanol producing yeast, *E. coli* strain KO11, or other bacteria or fungi, followed by distillation to recover ethanol. The solids residue remaining may still be utilized as a cattle feed product, having a higher protein content than the citrus-based cattle feed currently being produced, and retaining the health promoting flavonoids contained in citrus peel. Alternatively, the solids residue after distillation may also be pressed and filtered with optional recovery of acetate, five carbon sugars, or galacturonic acid monomers/polymers from the filtrate. Both steam stripping or centrifugation and hydrolysis work more efficiently if the raw solid citrus processing waste is ground to a particle size of less than about one inch (e.g., less than one inch; preferably less than about one-half inch (e.g., less than one-half inch)) using a hammer mill, grinding pump or similar shredding/chopping/grinding apparatus capable of handling and reducing said waste to the required size; such equipment is well known in the art. A progressing cavity pump or similar pump (or conveyor) capable of pumping/moving raw or ground peel waste with dry solids content up to thirty-five percent is then used to feed and mix the material (resulting from steam stripping and cooling) during the enzymatic hydrolysis and fermentation.

In a preferred processing embodiment the particle size of solids in the raw solid citrus waste is reduced to a size sufficient for further processing, then the ground peel is heated to a range of about 80° to about 240° C. (e.g., 80° to 240° C.; preferred range about 100° to about 160° C. (100° to 160° C.)) by direct steam injection (et cooker), passage through a heated hollow shaft screw conveyer or other direct or indirect heating device at a pressure between about 0 to about 150 psi (e.g., 0-150 psi; preferred range about 10 to about 100 psi (e.g., 10-100 psi), more preferred range about 20 to about 80 psi (e.g., 20-80 psi)), and then released into a flash tank at a reduced pressure where the limonene and condensed steam vaporize and are removed to the condenser. Heating by steam injection and sudden decompression has the benefit of a simultaneous or sequential shearing and disintegration action which is beneficial to the subsequent enzymatic hydrolysis process. The heating causes the limonene content to be decreased through evaporation and steam stripping with additional limonene being removed during vacuum cooling. The limonene is then recovered by condensation of the removed steam and decanting (or centrifuging) the recovered liquid to separate immiscible water and limonene layers. The solid or semi-solid and highly viscous citrus waste is then cooled and adjusted for pH, followed by sequential or simultaneous hydrolysis and fermentation using an enzyme mixture and fermentation organisms such as yeast, *E. coli* strain KO11, or other bacteria or fungi, in an agitated system with mixing accomplished using high solids pumps or high solids mixers to facilitate hydrolysis and fermentation. After fermentation, the ethanol is separated by distillation and the resulting residue can then be pressed and dried for use as cattle feed or further processed with fermentation using *E. Coli* KO11, or other bacteria or fungi, to produce more ethanol and acetate, or the unfermented galacturonic acid monomers/polymers and five carbon sugars may be recovered as additional products. While the method described herein is unique in converting solid citrus juice processing waste which is high in pectin and other complex carbohydrates, making it difficult to handle, it can also be used to convert other processing waste materials with chemical compositions similar to citrus waste, such as sugar beet bagasse, containing large amounts of pectin and which are also difficult to handle in processing without adding large volumes of water.

SUMMARY OF THE INVENTION

The primary object of the present invention is to provide a method and system for producing ethanol from solid citrus processing waste.

Another object of the present invention is to increase the recovery of limonene from citrus waste in order to reduce pollution from limonene that results when raw citrus waste is converted into cattle feed by current drying processes.

A further object of the present invention is to increase the recovery of limonene from citrus waste in order be sold as a high value byproduct.

A further object of the present invention is to provide such a method that produces ethanol and byproducts, preferably for a lower cost than ethanol produced from current methods.

An even further object of the present invention is to provide a method that yields other byproducts including five carbon sugars, galacturonic monomers/polymers, and a citrus based feed product for cattle and pets that has higher protein content and value than the citrus based cattle feed made from current processes.

The present invention fulfills the above and other objects by providing a method and system for producing ethanol from solid citrus waste that reduces limonene in the citrus peel in order that fermentation can take place to yield ethanol. This system includes means for reducing the particle size of solid citrus waste to a pre-determined size when necessary for processing, utilizing a hammer mill, grinding pump or similar shredding/chopping/grinding apparatus. Limonene may be then removed using the following technique: The solid citrus waste is heated and partially pre-hydrolyzed at or above atmospheric pressure using a jet cooker, extruder, or other direct or indirect heating device, which also pasteurizes the waste. The hot citrus waste (which is solid or semi-solid and highly viscous) is then passed through a hold tube of a designed diameter and length to maintain the heated and flowing material at the desired temperature for about 1 to about 20 minutes (e.g., 1-20 minutes) to soften and degrade cell wall materials. The heated material is then passed into a flash tank or tube with a drop in pressure from that of the hold tube which causes vaporization of the limonene and some water. The water and limonene vapors are removed and recovered by condensation into a separate tank. The solid or semi-solid and highly viscous material are then pumped out of the flash tank and rapid cooling of the hot waste can be achieved by a single or multistage vacuum cooling which gives the additional benefit of further limonene and water removal; the solid or semi-solid and highly viscous hot citrus waste becomes a solid material after cooling. However, other direct or indirect heat exchange methods can be used for cooling and stripping the solid citrus waste. The pH is also adjusted to a suitable range for enzymes and microorganisms by the addition of acids or bases. Simultaneous or sequential hydrolysis and fermentation are then accomplished by the addition of hydrolytic enzymes with or without simultaneous addition of ethanol producing microorganisms such as fungi, yeasts or bacteria. Hydrolysis and/or fermentation of the highly viscous citrus solids may be accomplished using an enzyme mixture while citrus solids are circulated using high solids pumps or mixed using a high solids mixer or agitator which liquefies the highly viscous mixture. Finally, ethanol can be distilled from the liquefied and fermented citrus waste/beer. Optionally and additionally, the resulting residue can be further processed into solids and pet or cattle feed using a centrifuge and/or press and drying devices. Furthermore, the residue may also yield acetate, galacturonic acid monomers and polymers, and five carbon sugars. The pH of the citrus waste is controlled throughout the process in the range of pH about 1 to about 13 (e.g., pH 1-13; preferred pH range about 3 to about 9 (e.g., pH 3-9), more preferred pH range about 3 to about 7 (e.g., pH 3-7) by addition of acids/bases to optimize the hydrolysis by enzymes and/or physically/chemically during heating and to optimize fermentation outputs.

The above and other objects, features and advantages of the present invention should become even more readily apparent to those skilled in the art upon a reading of the following detailed description in conjunction with the drawings wherein there is shown and described illustrative embodiments of the invention.

DESCRIPTION OF THE PREFERRED EMBODIMENTS

Figure 1:
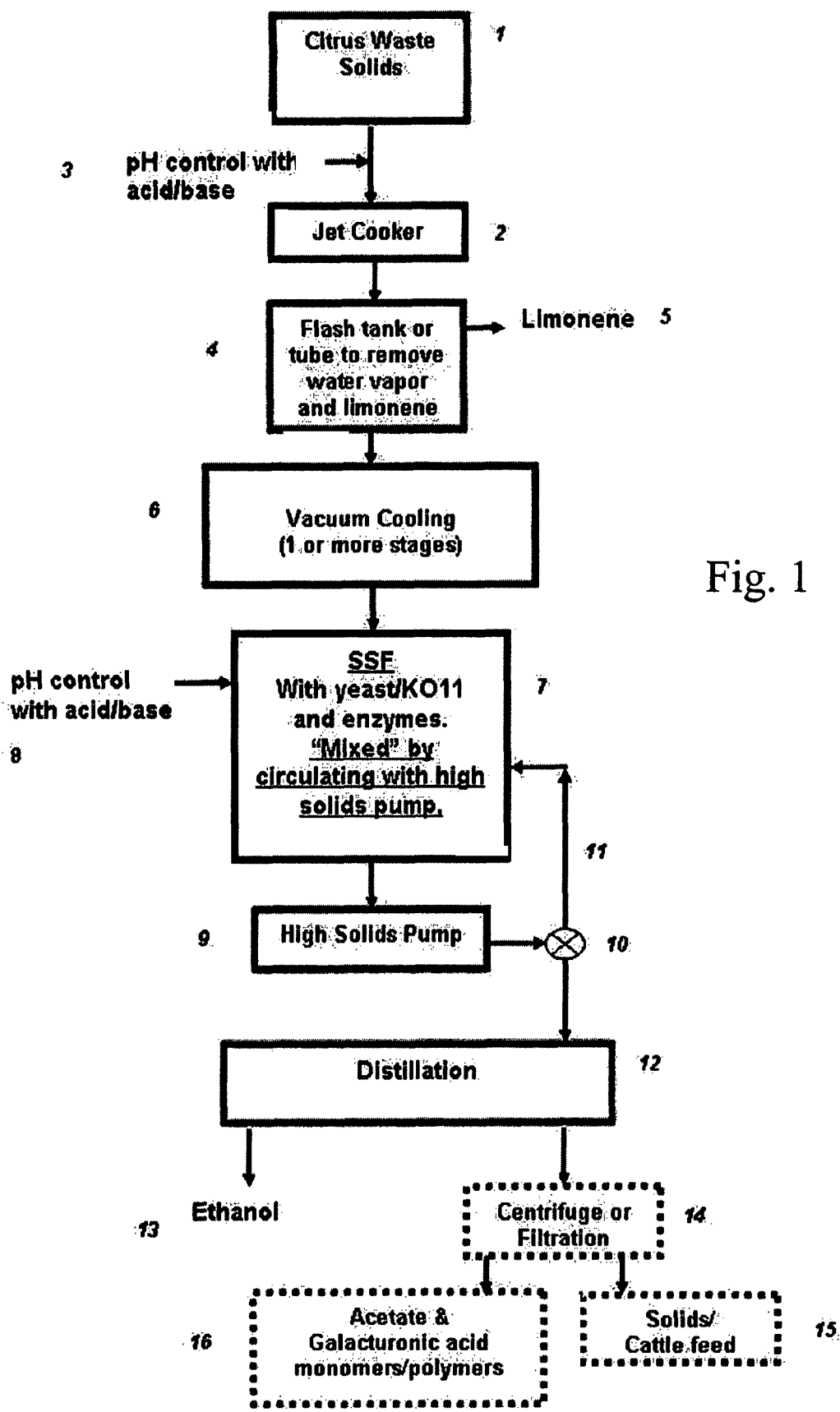
FIG. 1 shows a block diagram illustrating the ethanol process of the present invention in which limonene is removed by heating using a jet cooker and flash tube/tank prior to fermentation.
Figure 3:
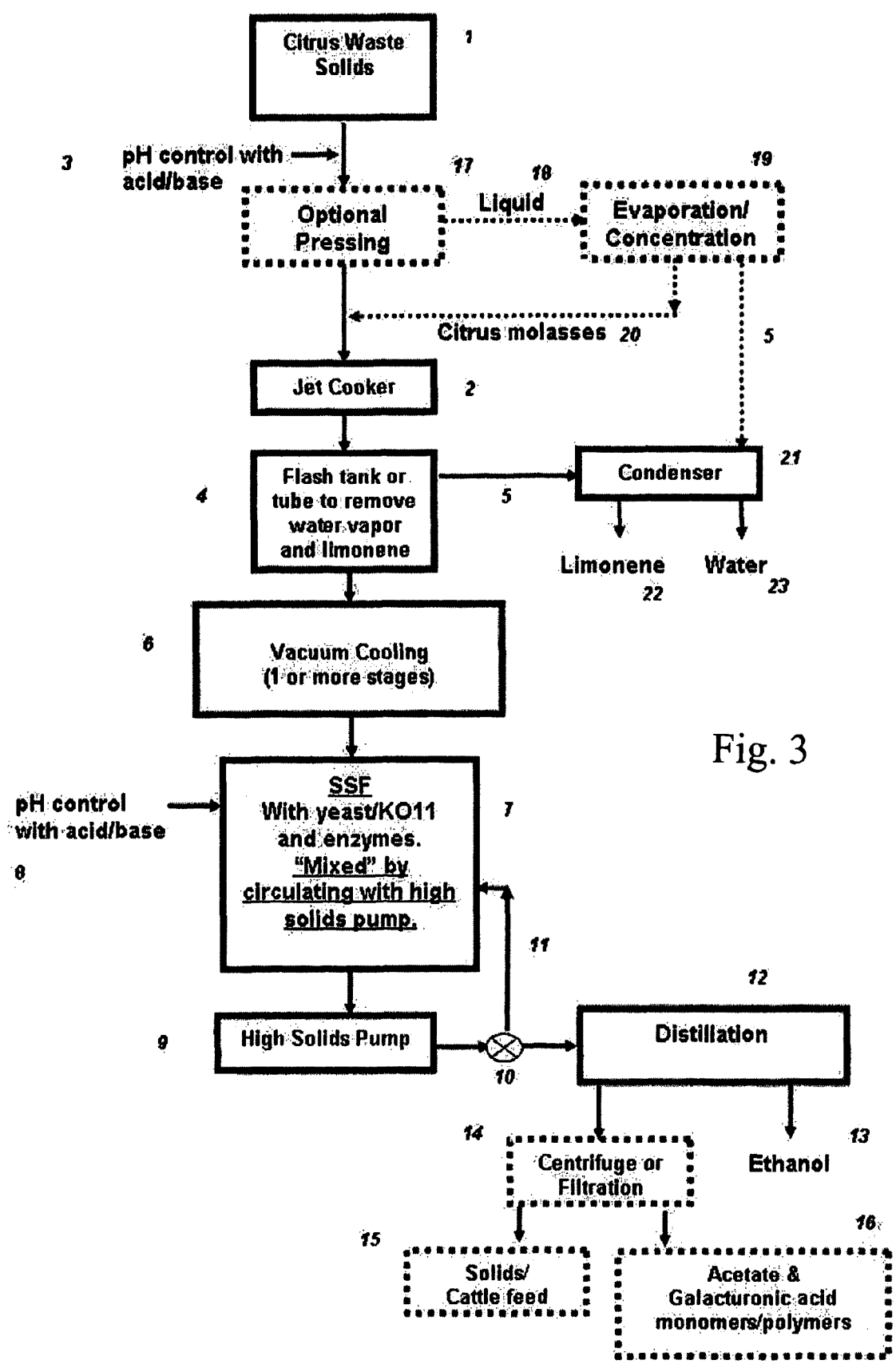
FIG. 3 shows a block diagram illustrating the ethanol process of the present invention in which the citrus waste solids are optionally pressed.

For purposes of describing the preferred embodiment, the terminology used in reference to the numbered components in FIGS. 1 and 3 is as follows:
1. Citrus waste solids (preferably ground)
2. Jet cooker
3. pH control
4. Flash tube or tank
5. Limonene/steam vapor
6. Vacuum tank
7. Fermentation mixing tank
8. pH control
9. High solids pump
10. Valve
11. Return line
12. Distillation
13. Ethanol
14. Centrifuge or filtration
15. Solids/cattle feed
16. Acetate, 5C sugars, GA polymers
17. Optional screw press
18. Pressed liquor
19. Evaporator
20. Concentrated molasses
21. Condenser
22. Limonene
23. Water With reference to the drawings, a preferred embodiment of the ethanol production process is shown in FIG. 1 in which separation of the limonene in citrus waste is accomplished via heating and rapid cooling. FIG. 1 begins with citrus waste solids (solid citrus waste) 1, in which the citrus solids, consisting primarily of citrus peel, may be preferably reduced to a pre-determined size for processing, generally less than one-half inch, by shredding/chopping/grinding apparatus. The pH of the citrus solids may be adjusted to the range of pH 1 to 13 (preferred pH 2 to 9) 3 before being heated to a temperature between 80° to 240° C. (preferred range 100° to 160° C.) by jet cooker (steam injection) 2 or alternatively by passing through a heated hollow shaft screw conveyer or similar direct or indirect heating device. Then the solid or semi-solid and highly viscous waste is injected through a backpressure valve and venturi tube into a flash tube or tank 4 where the water vapor containing limonene 5 is separated; the removed vapor is then condensed into a decanter and limonene run off as a liquid from the top layer. A vacuum cooling stage 6 (or other cooling device) can further reduce limonene content and rapidly cool the solid or semi-solid and highly viscous waste. Next the solid or semi-solid and highly viscous waste is pH adjusted 8 to pH 3 to 7 and then exposed to simultaneous hydrolysis and fermentation (or less preferably sequential hydrolysis and fermentation) utilizing enzymes and ethanol-producing yeasts, E. coli strain KO11, or other ethanol producing organisms such as fungi, E. coli, or Z. mobilis, in a fermentation mixing tank 7. The pH 8 may be adjusted. A high solids pump 9 re-circulates the waste through a valve 10 and return line 11 until sufficient fermentation has been achieved to produce significant ethanol concentration in the waste. As an alternative, the waste may be mixed with a high solids mixer/auger. Once sufficient ethanol concentration is attained the waste proceeds to distillation 12, or equivalent separation technology, in which ethanol 13 is separated from the waste. The residue remaining after distillation can then be processed using a centrifuge 14 or filtration device to separate the solids from liquid. Thereafter the solids can be dried for use in making a cattle feed 15 and the liquid can also be further fermented using E. coli KO11 or other ethanol producing organisms to produce additional ethanol and acetate and/or processed to produce galacturonic acid monomer/polymers or other products 16.

Figure 2:
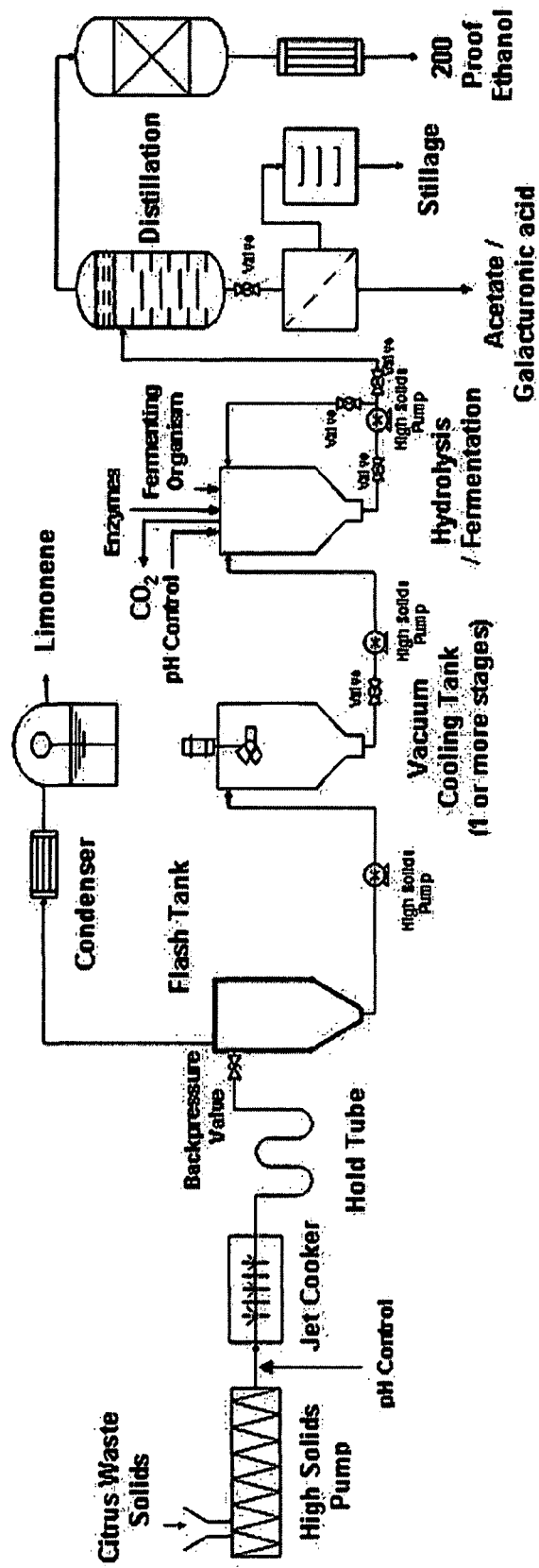
FIG. 2 shows a flow diagram of a typical process according to this invention.

In FIG. 2, the citrus waste solids are transferred to the jet cooker via a high solids pump; a positive displacement pump with an optional incorporated grinding/chopping mechanism and capable of moving high solids mixtures against pressures to 200 psi may be utilized. Pumped solid citrus waste is heated to 80°-240° C. (100°-160° C. preferred) under pressure using steam injection (jet cooker) and held for about 2 to about 20 minutes (e.g., 2-20 minutes) under pressure at about 0 to about 150 psi (e.g., 0-150 psi; preferred about 10 to about 100 psi (e.g., 10-100 psi), more preferred range about 20 to about 80 psi (e.g., 20-80 psi)) to soften and degrade cell structural without allowing vaporization and a phase change of contained moisture. Pressure is maintained through the use of an adjustable back pressure valve or by situating the flash tank at a sufficient height such that the weight of the material in the vertical column maintains the desired pressure diferential. Phase change prevention of contained moisture is critical to attaining the desired pretreatment temperatures efficiently with minimal energy input. The treated material under pressure is then released into a flash tank at atmospheric or reduced pressure (about −10 to about 0 psi (e.g., −10 to 0 psi)) causing the limonene (90% or more contained in the waste) and a part of the water to volatilize and escape through a vent to a condenser where the limonene is recovered by condensation and collected off the top of the water layer that also collects. The flashing further breaks apart and cools the solid or semi-solid and highly viscous citrus waste to about 95° to about 98° C. (e.g., 95°-98° C.). The treated solids collect at the bottom of the flash tank from where they are pumped using a high solids pump to one or more (arranged in series) vacuum cooling tanks (devices) where they are cooled under vacuum to less than about 40° C. (e.g., less than 40° C.), a temperature suitable for enzyme hydrolysis and fermentation. Vacuum cooling also removes part of the limonene and condensed steam from the stripping step and increases concentration of sugars in treated waste. The cooled solids are then hydrolyzed and fermented to produce ethanol. Sugar beet bagesse can be treated in a similar manner (though there in no limonene to be removed).

FIG. 3 is similar to FIG. 1 except that a base (e.g., calcium oxide) to added to the solid citrus waste which is then pressed to form pressed waste and citrus press liquor. The citrus press liquor is then sent to an evaporator to produce citrus molasses and a vapor containing water and limonene. The citrus molasses is then added back to the pressed waste which is then sent to the jet cooker to be treated as in FIG. 1. The pressed waste with citrus molasses added back produces material containing a higher solids and sugar content which will then yield fermented mash with 6-8% ethanol after treatment and fermentation.

The jet cooker which may be utilized in the present invention is not equivalent to a fuel fired heater since the jet cooker provides additional mixing and shear which cannot be accomplished by direct fired heater. In addition, direct fired heaters can only be operated with liquids. Furthermore, many types of equipment suitable for use with liquids or slurries are not suitable for use with solids or highly viscous materials.

Solid citrus waste and citrus waste solids in the present invention refer to wet citrus waste containing primarily peel, membranes, and seeds, which result from the processing of citrus fruit for juice. This material is of such a composition that there is no continuous liquid phase between waste particles and liquid is soaked into the particles. Such a material is not a slurry, liquid mixture, or suspension. In the present invention, a slurry may only occur during enzymatic hydrolysis and fermentation. Processing of such a difficult material (i.e., solid citrus waste) is novel and to our knowledge has not been disclosed in the prior art.

Thus, the present invention as described and illustrated teaches a system whereby solid citrus processing waste can be efficiently converted into ethanol and other byproducts. Although only a few embodiments of the present invention have been described in detail hereinabove, all improvements and modifications to this invention within the scope or equivalents of the claims are included as part of this invention.

All of the references cited herein are incorporated by reference in their entirety. Also incorporated by reference in their entirety are the following U.S. patent applications: Ser. No. 11/599,056 (Method And Apparatus For Vacuum Cooling Of Viscous Mixtures) filed on 14 Nov. 2006; Ser. No. 11/603,277 (Method And System Of Pretreating Citrus Waste) filed on 21 Nov. 2006.

Thus, in view of the above, the present invention concerns (in part) the following:

A method of producing ethanol from (solid) citrus waste, said method comprising (or consisting essentially of or consisting of) heating solid citrus waste to form heated citrus waste and a vapor containing water and peel oil components, separating said heated citrus waste and said vapor containing water and peel oil components to produce separated heated citrus waste and separated vapor containing water and peel oil components, cooling said separated heated citrus waste to form cooled citrus waste, and simultaneously or sequentially hydrolyzing and fermenting said cooled citrus waste to produce ethanol; said method comprising optionally reducing the particle size of said solid citrus waste prior to said heating. The above method, wherein said heating is at about 80° to about 240° C. or is at about 100° to about 160° C.

The above method, wherein said heating is direct heating.

The above method, wherein said heating utilizes a jet cooker.

The above method, wherein said separating utilizes a flash tank or tube.

The above method, wherein said cooling utilizes single stage or multistage vacuum cooling. Wherein said cooling utilizes multistage vacuum cooling.

The above method, wherein the concentration of limonene in said cooled citrus waste is below about 3,000 ppm or below about 1,500 ppm.

The above method, wherein said hydrolyzing comprises adding enzymes to said cooled citrus waste. Wherein said enzymes are selected from the group consisting of pectinase, hemicellulases, cellulases, beta-glucosidases and mixtures thereof.

The above method, said method further comprising reducing the particle size of said solid citrus waste prior to said heating. Wherein said particle size being less than about one inch or less than about one-half inch.

The above method, wherein water is added in said method only in the form of steam during said heating.

The above method, wherein less than about 0.3 lbs water is added per pound of solid citrus waste. Wherein less than about 0.15 lbs water is added per pound of solid citrus waste. Wherein less than about 0.1 lbs water is added per pound of solid citrus waste.

The above method, wherein said method does not involve the addition of carbon dioxide or carbonic acid.

The above method, wherein said method does not involve pressing of said solid citrus waste.

The above method, wherein said method does not involve a screw press.

A method of producing ethanol from (solid) citrus waste, said method comprising (or consisting essentially of or consisting of) adding a base (e.g., calcium oxide) to said solid citrus waste, pressing said solid citrus waste to form citrus press liquor and pressed waste, evaporating water from said citrus press liquor to form citrus molasses, adding said citrus molasses to said pressed waste and heating to form heated citrus waste and a vapor containing water and peel oil components, separating said heated citrus waste and said vapor containing water and peel oil components to produce separated heated citrus waste and separated vapor containing water and peel oil components, cooling said separated heated citrus waste to form cooled citrus waste, and simultaneously or sequentially hydrolyzing and fermenting said cooled citrus waste to produce ethanol; said method comprising optionally reducing the particle size of said solid citrus waste prior to said heating.

A method of producing ethanol from (solid) sugar beet bagasse, said method comprising heating sugar beet bagasse to form heated sugar beet bagasse and a vapor containing water, separating said heated sugar beet bagasse and said vapor containing water to produce separated sugar beet bagasse and separated vapor containing water, cooling said separated sugar beet bagasse to form cooled sugar beet bagasse, and simultaneously or sequentially hydrolyzing and fermenting said cooled sugar beet bagasse to produce ethanol; said method comprising optionally reducing the particle size of said sugar beet bagasse prior to said heating.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A method of producing ethanol from solid citrus waste, said method comprising (i) optionally reducing the particle size of said solid citrus waste prior to heating, (ii) heating said solid citrus waste by direct steam injection at a temperature of about 80° to about 240° C. to form heated citrus waste and a vapor containing water and peel oil components, (iii) separating said heated citrus waste and said vapor containing water and peel oil components to produce separated heated citrus waste and separated vapor containing water and peel oil components by releasing said heated citrus waste and said vapor containing water and peel oil components into a flash tank or flash tube at a pressure lower than (ii), (iv) cooling said separated heated citrus waste to form cooled solid citrus waste, (v) simultaneously or sequentially hydrolyzing and fermenting said cooled solid citrus waste to produce ethanol and residue wherein said hydrolyzing involves adding hydrolytic enzymes to said cooled solid citrus waste, and (vi) separating said alcohol from said residue; wherein water is added in said method only in the form of steam during said heating.

2. The method according to claim 1, wherein said heating is at about 100° to about 160° C.

3. The method according to claim 1, wherein said heating utilizes a jet cooker.

4. The method according to claim 1, wherein said cooling utilizes single stage or multistage vacuum cooling.

5. The method according to claim 1, wherein said cooling utilizes multistage vacuum cooling.

6. The method according to claim 1, wherein the concentration of limonene in said cooled solid citrus waste is below about 3,000 ppm.

7. The method according to claim 1, wherein the concentration of limonene in said cooled solid citrus waste is below about 1,500 ppm.

8. The method according to claim 1, wherein said enzymes are selected from the group consisting of pectinases, hemicellulases, cellulases, beta-glucosidases and mixtures thereof.

9. The method according to claim 1, said method comprising (i) reducing the particle size of said solid citrus waste to less than about one inch prior to heating.

10. The method according to claim 1, said method comprising (i) reducing the particle size of said solid citrus waste to less than about one-half inch prior to heating.

11. The method according to claim 1, wherein less than about 0.3 lbs water is added per pound of solid citrus waste.

12. The method according to claim 1, wherein less than about 0.15 lbs water is added per pound of solid citrus waste.

13. The method according to claim 1, wherein less than about 0.1 lbs water is added per pound of solid citrus waste.

14. The method according to claim 1, comprising (ii) heating solid citrus waste by direct steam injection at a temperature of about 80° to about 240° C. and a pressure of about 0 to about 150 psi to form heated citrus waste and a vapor containing water and peel oil components.

15. The method according to claim 1, comprising (ii) heating said solid citrus waste by direct steam injection at a temperature of about 100° to about 160° C. and a pressure of about 10 to about 100 psi to form heated citrus waste and a vapor containing water and peel oil components.

16. The method according to claim 1, comprising (ii) heating said solid citrus waste by direct steam injection at a temperature of about 100° to about 160° C. and a pressure of about 20 to about 80 psi to form heated citrus waste and a vapor containing water and peel oil components.

17. The method according to claim 1, comprising (v) simultaneously hydrolyzing and fermenting said cooled solid citrus waste to produce ethanol and residue.

18. The method according to claim 1, wherein the pH of said citrus waste is controlled throughout said method at a pH of about 3 to about 7.

19. The method according to claim 1, wherein the pH of said cooled solid citrus waste is adjusted to a pH of 3 to 7.

20. The method according to claim 1, wherein said heated citrus waste and said vapor containing water and peel oil components are passed through a hold tube before entering said flash tank or said flash tube at a pressure lower than said hold tube.

21. The method according to claim 1, comprising (ii) heating solid citrus waste by direct steam injection at a temperature of about 80° to about 240° C. and a pressure of about 0 to about 150 psi for about 1 to about 20 minutes to form heated citrus waste and a vapor containing water and peel oil components.

22. The method according to claim 1, wherein said method consists essentially of (i) optionally reducing the particle size of said solid citrus waste prior to heating, (ii) heating said solid citrus waste by direct steam injection at a temperature of about 80° to about 240° C. to form heated citrus waste and a vapor containing water and peel oil components, (iii) separating said heated citrus waste and said vapor containing water and peel oil components to produce separated heated citrus waste and separated vapor containing water and peel oil components by releasing said heated citrus waste and said vapor containing water and peel oil components into a flash tank or flash tube at a pressure lower than (ii), (iv) cooling said separated heated citrus waste to form cooled solid citrus waste, and (v) simultaneously or sequentially hydrolyzing and fermenting said cooled solid citrus waste to produce ethanol and residue wherein said hydrolyzing involves adding hydrolytic enzymes to said cooled solid citrus waste, and (vi) separating said alcohol from said residue; wherein water is added in said method only in the form of steam during said heating.

23. The method according to claim 1, wherein said method consists of (i) optionally reducing the particle size of said solid citrus waste prior to heating, (ii) heating said solid citrus waste by direct steam injection at a temperature of about 80° to about 240° C. to form heated citrus waste and a vapor containing water and peel oil components, (iii) separating said heated citrus waste and said vapor containing water and peel oil components to produce separated heated citrus waste and separated vapor containing water and peel oil components by releasing said heated citrus waste and said vapor containing water and peel oil components into a flash tank or flash tube at a pressure lower than (ii), (iv) cooling said separated heated citrus waste to form cooled solid citrus waste, and (v) simultaneously or sequentially hydrolyzing and fermenting said cooled solid citrus waste to produce ethanol and residue wherein said hydrolyzing involves adding hydrolytic enzymes to said cooled solid citrus waste, and (vi) separating said alcohol from said residue; wherein water is added in said method only in the form of steam during said heating.

24. The method according to claim 1, wherein said solid citrus waste contains peel, membranes, and seeds resulting from the processing of citrus fruit for juice.

25. The method according to claim 24, wherein there is no free liquid between the solid pieces of said solid citrus waste.

26. The method according to claim 24, wherein said method comprises (i) optionally reducing the particle size of said solid citrus waste prior to heating, (ii) heating said solid citrus waste by direct steam injection at a temperature of about 80° to about 240° C. to form heated solid or semi-solid and highly viscous citrus waste and a vapor containing water and peel oil components, (iii) separating said heated solid or semi-solid and highly viscous citrus waste and said vapor containing water and peel oil components to produce separated heated solid or semi-solid and highly viscous citrus waste and separated vapor containing water and peel oil components by releasing said heated solid or semi-solid and highly viscous citrus waste and said vapor containing water and peel oil components into a flash tank or flash tube at a pressure lower than (ii), (iv) cooling said separated heated solid or semi-solid and highly viscous citrus waste to form cooled solid citrus waste, (v) simultaneously or sequentially hydrolyzing and fermenting said cooled solid citrus waste to produce ethanol and residue wherein said hydrolyzing involves adding hydrolytic enzymes to said cooled solid citrus waste, and (vi) separating said alcohol from said residue; wherein water is added in said method only in the form of steam during said heating.

* * * * *